US006375616B1

(12) United States Patent
Soferman et al.

(10) Patent No.: US 6,375,616 B1
(45) Date of Patent: Apr. 23, 2002

(54) AUTOMATIC FETAL WEIGHT DETERMINATION

(75) Inventors: Ziv Soferman, Givatayim; Michael Berman, Har Adar, both of (IL)

(73) Assignee: Biomedicom Ltd., Jerusalem (IL)

( * ) Notice: Subject to any disclaimer, the term of this patent is extended or adjusted under 35 U.S.C. 154(b) by 0 days.

(21) Appl. No.: 09/709,796

(22) Filed: Nov. 10, 2000

(51) Int. Cl.$^7$ .................................................. A61B 8/00

(52) U.S. Cl. ........................ 600/443; 128/916; 128/922

(58) Field of Search ................................ 600/437, 443, 600/447; 128/916, 922

(56) References Cited

U.S. PATENT DOCUMENTS

| | | | |
|---|---|---|---|
| 4,898,179 A | | 2/1990 | Sirota .......................... 128/670 |
| 5,315,512 A | | 5/1994 | Roth ...................... 364/413.25 |
| 5,588,435 A | * | 12/1996 | Weng et al. ................. 600/443 |
| 5,605,155 A | | 2/1997 | Chalana et al. ......... 128/660.07 |
| 5,608,849 A | * | 3/1997 | King, Jr. ..................... 382/128 |
| 5,626,133 A | * | 5/1997 | Johnson et al. ............. 600/437 |
| 5,777,905 A | | 7/1998 | Dowdle ................. 364/709.12 |
| 5,795,296 A | * | 8/1998 | Pathak et al. ............... 600/443 |
| 5,797,396 A | * | 8/1998 | Geiser et al. ............... 600/407 |
| 5,838,592 A | * | 11/1998 | Spratt .......................... 600/407 |
| 5,858,966 A | | 1/1999 | Harding et al. ................ 514/3 |

OTHER PUBLICATIONS

Thompson et al, "Estimation of Volume and Weight of the Perinate: Relationship to Morphometric Measurement by Ultrasonography", J. Ultrasound Med 2: 113–116 Mar. 1983.*

Liang et al, "Predicting Birth Weight by Fetal Upper-arm Volume with Use of Three-dimensional Ultrasonography", Am. Jrnl Obstetrics & Gynecology, vol. 177:635-8 Sep. 1997.*

Dudley et al, "A New Method for Fetal Weight Estimation Using Real-time Ultrasound", British Journal of Obstetrics and Gynaecology, vol. 94, pp 110–114, Feb. 1987.*

Shinozuka et al, "Fetal Weight Estimation by Ultrasound Measurement", Am. J. of Obstet. & Gynec. vol. 157:1140–1145, 1987 (Abstract).*

R. L. Deter et al., "Quantitative Obstetrical Ultrasonography", John Wiley & Sons, New York, 1986, pp. 115–116.

R. L. Goldberg et al., "Multilayer Piezoelectric Ceramics for Two–Dimensional Array Transducers", *IEEE Trans Ultrason. Ferro. Freq. Control*, vol. 41, No. 5, Sep. 1994, pp. 761–771.

E. J. Feleppa et al., "Two–Dimensional and Three–Dimensional Tissue–Type Imaging of the Prostate Based on Ultrasonic Spectrum Analysis and Neural–Network Classification", *Medical Imaging 2000: Ultrasonic Imaging and Processing*, 2000, pp. 152–160.

R. W. Prager et al., "Stradx: Real–Time Acquistion and Visualization of Freehand Three–Dimensional Ultrasound", *Medical Image Analysis*, 1998, vol. 3, No. 2, Oxford University Press, pp. 129–140.

(List continued on next page.)

*Primary Examiner*—Francis J. Jaworski
(74) *Attorney, Agent, or Firm*—Abelman, Frayne & Schwab

(57) ABSTRACT

This invention discloses an apparatus for fetal weight determination including an ultrasonic imager operative to image a fetus in utero and to provide output image data in respect thereof, an image processor operative automatically to measure at least one dimension of at least one fetal body part based on the output image data and to provide output body part dimension data, and an automatic fetal weight calculator operative to calculate fetal weight automatically based on the output body part dimension data. A method for determining fetal weight is also disclosed.

38 Claims, 11 Drawing Sheets

OTHER PUBLICATIONS

R. N. Rohling et al., "Radial Basis Function Interpolation for 3–D Ultrasound", Jul. 1998, Cambridge University Engineering Department, England, 27 pages.

A. Rosenfeld et al., "Digital Picture Processing", Second Edition, vol. 2, Academic Press, USA, 1982, pp. 84–113.

S.W. Smith et al., "Two–Dimensional Array Transducers Using Thick Film Connection Technology", *IEEE Trans. Ultrason. Ferro. Freq. Control*, vol. 40, No. 6, Nov. 1993, pp. 727–734.

Three & Six Degrees–of–Freedom Motion Trackers, Ascension Technology Corp. Product Catalogue, Burlington, Vermont, 2000, 3 pages.

"3–D Ultrasound, A Supplement to Diagnostic Imaging", Mar. 2000, San Francisco, CA, 23 pages.

Voluson 530D Digital 3D Sonography Device, Medison, Cypress, CA, 2000, 3 pages.

* cited by examiner-

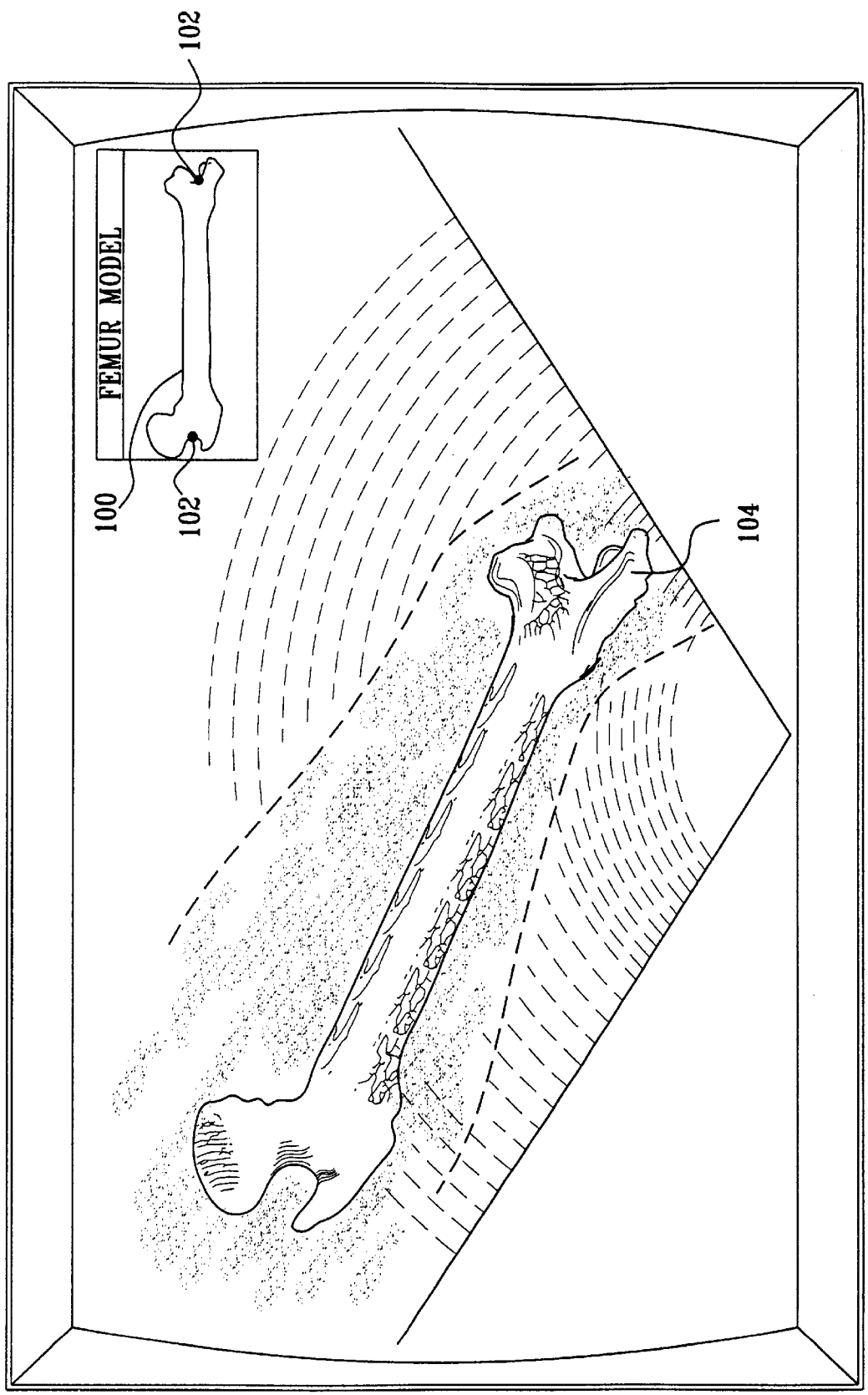

AUTOMATIC FETAL WEIGHT DETERMINATION

FIELD OF THE INVENTION

The present invention relates to fetal weight determination generally and more particularly to apparatus and methods for fetal weight determination employing ultrasonic imaging.

BACKGROUND OF THE INVENTION

Fetal weight determination is known using ultrasonic imaging techniques. The following U.S. Patents are believed to represent the state of the art: U.S. Pat. Nos. 5,626,133; 5,605,155 and 5,315,512;

SUMMARY OF THE INVENTION

The present invention seeks to provide an improved method and apparatus for automated fetal weight determination, which is capable of providing automatic or semi-automatic fetal weight indications.

There is thus provided in accordance with a preferred embodiment of the present invention apparatus for automated fetal weight determination including an ultrasonic imager which is operative to image a fetus in utero and to provide output image data in respect thereof, an image processor operates automatically to measure at least one dimension of at least one fetal body part based on the output image data and to provide output body part dimension data, and an automatic fetal weight calculator operative which is to calculate fetal weight automatically based on the output body part dimension data.

Further in accordance with a preferred embodiment of the present invention the image processor operates automatically to fit a three-dimensional model to the three-dimensional output image data, thereby to compensate for missing image data in the three-dimensional output image data.

There is thus provided in accordance with another preferred embodiment of the present invention apparatus for distinguishing a fetus in a three-dimensional ultrasound image of the fetus in utero, the apparatus including an ultrasonic imager operative to image a fetus in utero and to provide three-dimensional output image data in respect thereof, and an image processor operates automatically to distinguish the fetus from surrounding tissue based on the output image data.

There is thus provided in accordance with yet another preferred embodiment of the present invention apparatus for recognizing a fetal spine in an ultrasound image of the fetus in utero, the apparatus includes an ultrasonic imager operative to image a fetus in utero and to provide output image data in respect thereof, and an image processor which is operative automatically to recognize the fetal spine from surrounding tissue based on the output image data.

Further in accordance with a preferred embodiment of the present invention the image processor also operates to measure the length of the fetal spine.

There is thus provided in accordance with a further preferred embodiment of the present invention apparatus for automatically fitting a three-dimensional model of a fetus to a three-dimensional ultrasound image of the fetus in utero, the apparatus includes an ultrasonic imager operative to image a fetus in utero and to provide three-dimensional output image data in respect thereof, and an image processor which operates automatically to fit the three-dimensional model to the three-dimensional output image data.

Still further in accordance with a preferred embodiment of the present invention the image processor also operates automatically to fit portions of the three-dimensional model to corresponding portions of the three-dimensional output image data.

Additionally in accordance with a preferred embodiment of the present invention the image processor operates automatically to fit portions of the three-dimensional model of a fetal torso to corresponding portions of the three-dimensional output image data.

Further in accordance with a preferred embodiment of the present invention the image processor is also operative to provide mapping of anatomical markers from the model onto the output image data and to carry out measurements using the anatomical markers.

There is thus provided in accordance with a preferred embodiment of the present invention apparatus for automatically fitting a three-dimensional model of a fetus to a three-dimensional ultrasound image of the fetus in utero, the apparatus includes an image processor operative automatically to fit portions of the three-dimensional model to corresponding portions of the three-dimensional output image data.

Further in accordance with a preferred embodiment of the present invention the image processor also operates to provide mapping of anatomical markers from the model onto the output image data and to carry out measurements using the anatomical markers.

There is thus provided in accordance with a preferred embodiment of the present invention apparatus including an ultrasonic imager which operates to image a fetus in utero and to provide three-dimensional output image data in respect thereof, and an image processor which automatically fits the three-dimensional model of a fetal torso to the three-dimensional output image data.

Further in accordance with a preferred embodiment of the present invention the image processor also operates to provide mapping of anatomical markers from the model onto the output image data and to carry out measurements using the anatomical markers.

There is thus provided in accordance with yet another preferred embodiment of the present invention apparatus for automatically fitting a three-dimensional model of a fetal torso to a three-dimensional ultrasound image of the fetus in utero, the apparatus includes an image processor operative automatically to fit portions of the three-dimensional model of fetal torso to corresponding portions of the three-dimensional output image data.

Further in accordance with a preferred embodiment of the present invention the image processor also operates to provide mapping of anatomical markers from the model onto the output image data and to carry out measurements using the anatomical markers.

There is thus provided in accordance with yet another preferred embodiment of the present invention apparatus for automatically fitting a three-dimensional model of a fetal torso to a three-dimensional ultrasound image of the fetus in utero, the apparatus includes an ultrasonic imager which is operative to image a fetus in utero and to provide three-dimensional output image data in respect thereof, and an image processor which operates automatically to fit the three-dimensional model of a fetal torso to the three-dimensional output image data.

Further in accordance with a preferred embodiment of the present invention the image processor also operates to provide mapping of anatomical markers from the model onto the output image data and to carry out measurements using the anatomical markers.

There is thus provided in accordance with yet another preferred embodiment of the present invention apparatus for automatically fitting a three-dimensional model of a fetal torso to a three-dimensional ultrasound image of the fetus in utero, the apparatus includes an image processor operative automatically to fit portions of the three-dimensional model of fetal torso to corresponding portions of the three-dimensional output image data.

Further in accordance with a preferred embodiment of the present invention the image processor also operates to provide mapping of anatomical markers from the model onto the output image data and to carry out measurements using the anatomical markers.

There is thus provided in accordance with yet a further preferred embodiment of the present invention apparatus for fetal volume determination including an ultrasonic imager operative to image a fetus in utero and to provide output image data in respect thereof an image processor which operates automatically to measure at least one dimension of at least one fetal body part based on the output image data and to provide output body part dimension data, and an automatic fetal volume calculator operative to calculate fetal volume automatically based on the output body part dimension data.

There is thus provided in accordance with yet a further preferred embodiment of the present invention apparatus for fetal weight determination the apparatus includes an ultrasonic imager operative to image a fetus in utero and to provide output image data in respect thereof, an image processor operative which automatically measures at least one dimension of at least one fetal body part based on the output image data and provides output body part dimension data, a tissue characterization processor employing the output image data for providing data relating to percentages of different types of tissue in at least part of the fetus, and an automatic fetal weight calculator operative to calculate fetal weight automatically based on the output body part dimension data and the data relating to percentages of different types of tissue in at least part of the fetus.

There is thus provided in accordance with yet a further preferred embodiment of the present invention a method for determining fetal weight and includes: employing an ultrasonic imager to image a fetus in utero and to provide output image data in respect thereof, identifying at least one body part from the image data, employing an image processor to automatically measure at least one dimension of at least one fetal body part based on the output image data and to provide output body part dimension data, and calculating fetal weight automatically based on the output body part dimension data.

There is thus provided in accordance with yet a further preferred embodiment of the present invention a method for distinguishing a fetus in a three-dimensional ultrasound image of the fetus in utero, the method includes operating an ultrasonic imager to image a fetus in utero and to provide three-dimensional output image data in respect thereof, and provides an image processor to automatically distinguish the fetus from surrounding tissue based on the output image data.

There is thus provided in accordance with yet a further preferred embodiment of the present invention a method for recognizing a fetal spine in an ultrasound image of the fetus in utero, the method includes operating an ultrasonic imager to image a fetus in utero and to provide output image data in respect thereof, and provides an image processor to automatically recognize the fetal spine from surrounding tissue based on the output image data.

Further in accordance with a preferred embodiment of the present invention the image processor also operates to measure the length of the fetal spine.

There is thus provided in accordance with yet another further preferred embodiment of the present invention a method for automatically fitting a three-dimensional model of a fetus to a three-dimensional ultrasound image of the fetus in utero, the method includes employing an ultrasonic imager to image a fetus in utero and provides a three-dimensional output image data in respect thereof, provides a three-dimensional model, and employing an image processor to automatically fit the three-dimensional model to the three-dimensional output image data.

Further in accordance with a preferred embodiment of the present invention the image processor operates to automatically fit portions of the three-dimensional model to corresponding portions of the three-dimensional output image data.

Still further in accordance with a preferred embodiment of the present invention the image processor also operates to provide mapping of anatomical markers from the model onto the output image data and to carry out measurements on the output image data using the anatomical markers.

Additionally in accordance with a preferred embodiment of the present invention the image processor operates to automatically fit portions of the three-dimensional model of a fetal torso to corresponding portions of the three-dimensional output image data.

There is thus provided in accordance with yet another further preferred embodiment of the present invention a method for automatically fitting a three-dimensional model of a fetus to a three-dimensional ultrasound image of the fetus in utero, the method includes employing an image processor to automatically fit portions of the three-dimensional model to corresponding portions of the three-dimensional output image data.

Additionally in accordance with a preferred embodiment of the present invention the image processor operates automatically to fit a three-dimensional model to the three-dimensional output image data, thereby to compensate for missing image data in the three-dimensional output image data.

Further in accordance with a preferred embodiment of the present invention the image processor also operates to provide mapping of anatomical markers from the model onto the output image data and to carry out measurements on the output image data using the anatomical markers.

There is thus provided in accordance with yet another further preferred embodiment of the present invention a method for automatically fitting a three-dimensional model of a fetal torso to a three-dimensional ultrasound image of the fetus in utero, the method includes employing an ultrasonic imager to image a fetus in utero and provides three-dimensional output image data in respect thereof, and employs an image processor to automatically fit the three-dimensional model of a fetal torso to the three-dimensional output image data.

Further in accordance with a preferred embodiment of the present invention the image processor the image processor also operates to provide mapping of anatomical markers from the model onto the output image data and to carry out measurements on the output image data using the anatomical markers.

There is thus provided in accordance with yet another further preferred embodiment of the present invention a method for automatically fitting a three-dimensional model of a fetal torso to a three-dimensional ultrasound image of the fetus in utero, the method includes employing an image processor to automatically fit portions of the three-dimensional model of fetal torso to corresponding portions of the three-dimensional output image data.

Further in accordance with a preferred embodiment of the present invention the image processor the image processor also operates to provide mapping of anatomical markers from the model onto the output image data and to carry out measurements on the output image data using the anatomical markers.

There is thus provided in accordance with yet another further preferred embodiment of the present invention a method for automatically fitting a three-dimensional model of a fetal torso to a three-dimensional ultrasound image of the fetus in utero, the method includes employing an image processor to automatically fit portions of the three-dimensional model of fetal torso to corresponding portions of the three-dimensional output image data.

Further in accordance with a preferred embodiment of the present invention the image processor the image processor also operates to provide mapping of anatomical markers from the model onto the output image data and to carry out measurements on the output image data using the anatomical markers.

There is thus provided in accordance with a further preferred embodiment of the present invention a method for fetal volume determination, the method includes employing an ultrasonic imager to image a fetus in utero and to provide output image data in respect thereof, identifying at least one individual fetal body part from the image data, providing an image processor to automatically measure at least one dimension of at least one fetal body part based on the output image data and to provide output body part dimension data, and employing an automatic fetal volume calculator to calculate fetal volume automatically based on the output body part dimension data.

There is thus provided in accordance with a further preferred embodiment of the present invention a method for fetal weight determination includes operating an ultrasonic imager to image a fetus in utero and to provide output image data in respect thereof, identifying at least one individual fetal body part from the image data, providing an image processor to automatically measure at least one dimension of at least one fetal body part based on the output image data and to provide output body part dimension data, providing a tissue characterization processor employing the output image data for providing data relating to percentages of different types of tissue in at least part of the fetus, and operating an automatic fetal weight calculator to calculate fetal weight automatically based on the output body part dimension data and the data relating to percentages of different types of tissue in at least part of the fetus.

BRIEF DESCRIPTION OF THE DRAWINGS

The present invention will be understood and appreciated more fully from the following detailed description, taken in conjunction with the drawings in which:

FIGS. 8A, 8B and 8C illustrate typical steps useful in the mapping of a femur model and markers onto an ultrasound image of a femur bone;

DETAILED DESCRIPTION OF A PREFERRED EMBODIMENT

Figure 1:
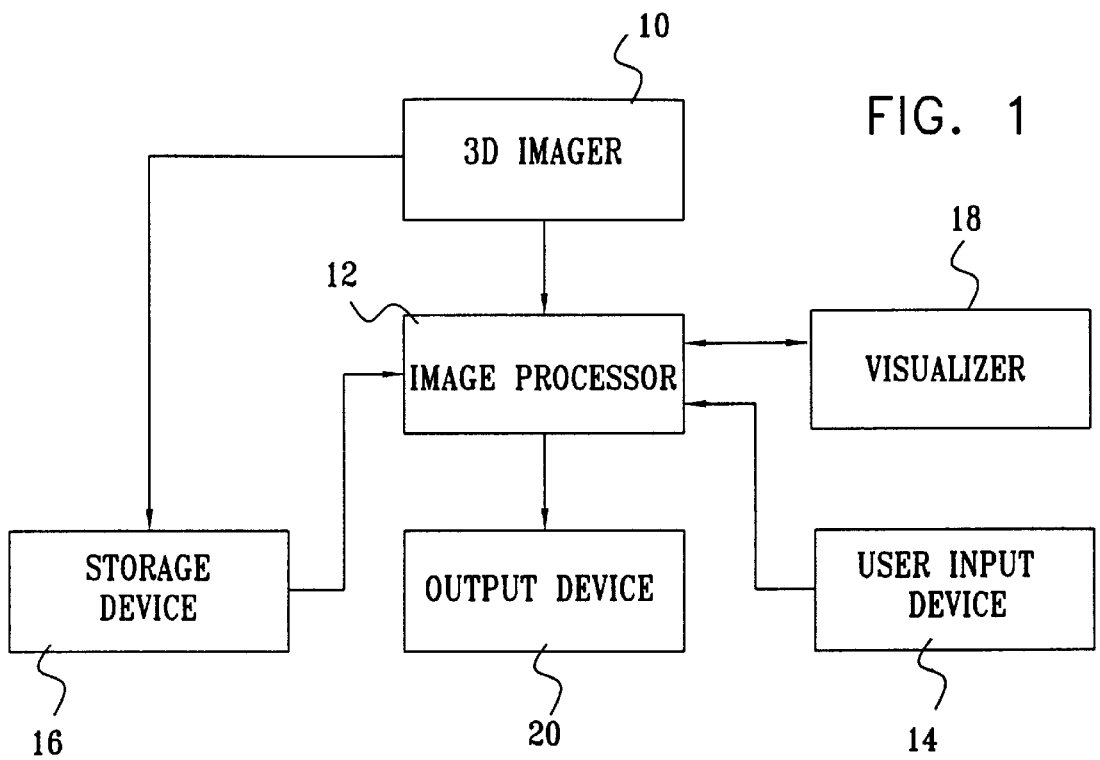
FIG. 1 is a simplified block diagram illustration of a system for automated fetal weight determination, constructed and operative in accordance with a preferred embodiment of the present invention.

Reference is now made to FIG. 1, which is a simplified block diagram illustration of a system for automated fetal weight determination, constructed and operative in accordance with a preferred embodiment of the present invention. As seen in FIG. 1, the system preferably comprises a three-dimensional ultrasound imager 10, such as a direct 3D imager, for example as described in "Two-Dimensional Array Transducers Using Thick Film Connection Technology", S. W. Smith and E. D. Light, IEEE Trans. Ultrason. Ferro. Freq. Control, UFFC-40, 727–734, 1993; and "Multilayer Piezoelectric Ceramics for Two-Dimensional Array Transducers", R. L. Goldberg and S. W. Smith, IEEE Trans. Ultrason. Ferro. Freq. Control, UFFC-41, 761–771, 1994, the disclosures of which are hereby incorporated by reference, or a 2D imager combined with a 3D constructor, for example the "Voluson 530D™", system commercially available from Medison America Inc., Cypress, Calif., USA.

The output of the imager 10, preferably in pixel or voxel form, is supplied to an image processor 12, which is described hereinbelow in greater detail with reference to FIG. 4. The image processor 12 also receives an input from a user interface 14 and from a storage device 16. The storage device 16, typically receives inputs from the 3D imager 10 and stores image data. Storage device 16 may also store geometrical models and associated parameters of one or more fetal body parts and may include archived clinical data. A visualizer 18, such as a color display, is preferably associated with the 3D imager 10, the image processor 12 and the user interface 14 and may provide an operator with a visually sensible indication of fetal images, as well as of the various functionalities of the image processor 12. The visualizer 18 preferably provides a 3D output.

The image processor 12 preferably includes software modules providing at least the following functionalities: image segmentation, measurement and weight calculations. Alternatively, the image processor 12 may not provide weight calculations, but instead may provide an operator with parameters which may be used by the operator to perform weight calculations.

The image processor 12 preferably provides an output to an output device 20, such as a display, printer or other output device. This output may also be communicated to a remote output device 20 via a computer network in any suitable manner.

Figure 2:
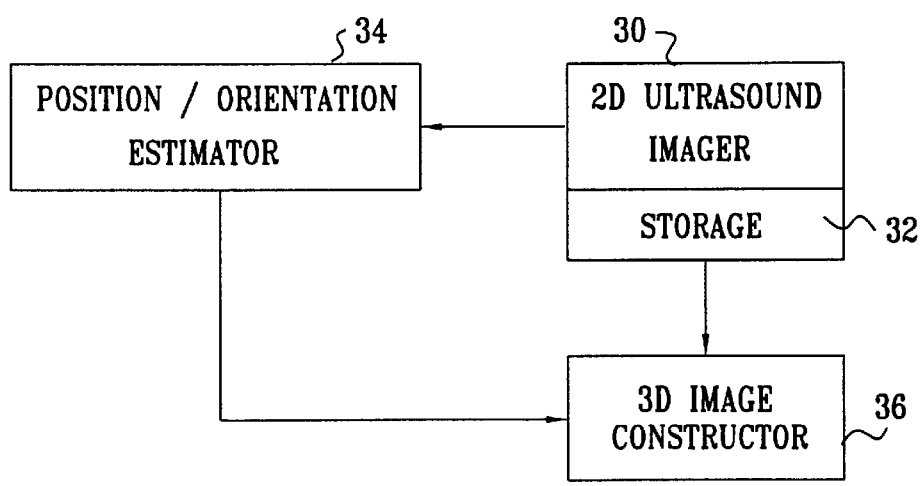
FIG. 2 is a simplified block diagram illustration of an imager forming part of the system of FIG. 1.

Reference is now made to FIG. 2, which is a simplified block diagram illustration of an imager forming part of the system of FIG. 1. FIG. 2 illustrates a 3D imager which is based on a 2D imager 30, such as the imaging system Voluson 530D™ available from Medison America Inc., Cypress, Calif., US. The 2D imager 30 is associated with an image data storage facility 32. Both imager 30 and storage facility 32 communicate with a position/orientation estimator 34. Estimator 34 is preferably operative to provide position orientation data for each of a plurality of 2D ultrasound images produced by the 2D imager 30. The estimator 34 may include a software or hardware position/orientation sensor such as "Three & Six Degrees-Of-Freedom Motion Trackers" available from 2000 Ascension Technology Corporation, P.O. Box 527, Burlington, Vt. 05402, USA.

A 3D image constructor 36 receives inputs from 2D imager 30, storage facility 32 and estimator 34 and provides a 3D image output to image processor 12 (FIG. 1).

It is appreciated that the functionality of FIG. 2 is provided by the above-mentioned 2D imaging "Voluson 530D™" system commercially available from Medison America Inc., Cypress, Calif., USA. An alternative to the functionality of FIG. 2 is the direct 3D imager, and based on the 2D phase array transducer, as described hereinabove.

Figure 3:
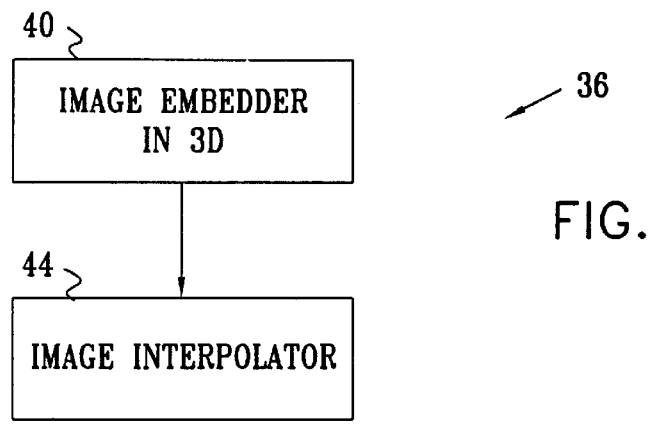
FIG. 3 is a simplified block diagram illustration of an image constructor forming part of the imager of FIG. 2.

Reference is now made to FIG. 3, which is a simplified block diagram illustration of an image constructor forming part of the imager of FIG. 2. As seen in FIG. 3, the image constructor 36 typically comprises a 3D image embedder 40, such as that described in "Stradx: Real-Time Acquisition and Visualization of Freehand Three-Dimensional Ultrasound" Medical Image Analysis (1998), Vol. 3, No. 2, pp 129–140, Richard W. Prager, Andrew Gee and Laurence Berman, published by Oxford University Press, the disclosure of which is hereby incorporated by reference, which outputs to an image interpolator 44, such as a that described in "Radial Basis Function Interpolation for 3-D Ultrasound" R. N. Rohling, A. H. Gee and L. Berman, CUED/F-INFENG/TR 327, July 1998, Cambridge University Engineering Department, Trumpington Street, Cambridge CB2 1PZ, England, the disclosure of which is incorporated by reference. The image embedder 40 employs position/orientation data provided by position/orientation estimator 34 (FIG. 2) to place slices within a 3D volume. The image constructor 36 places each 2D image in its place within a volumetric image to be constructed.

Figure 4:
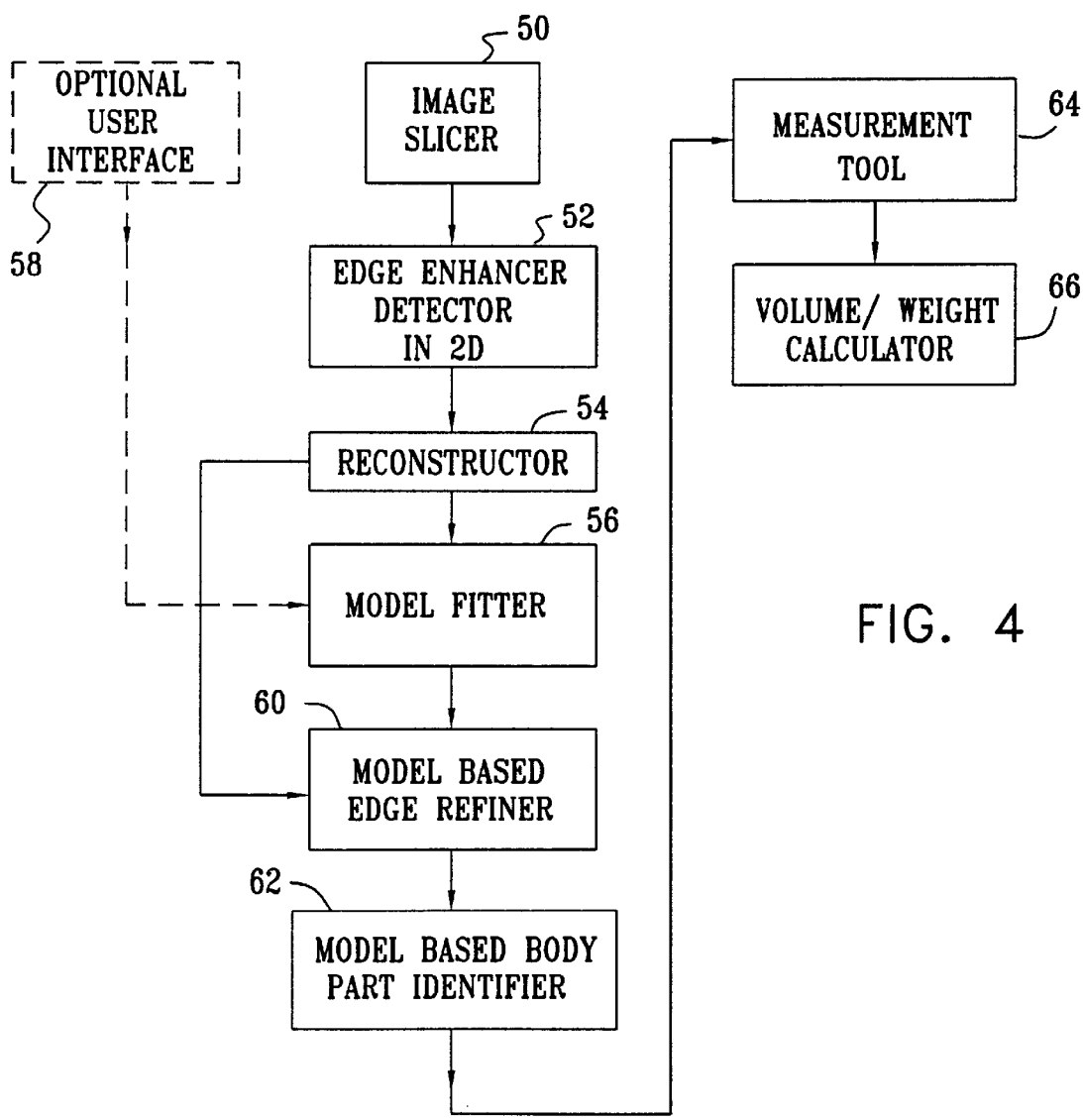
FIG. 4 is a simplified block diagram illustration of an image processor forming part of the system of FIG. 1.

Reference is now made to FIG. 4, which is a simplified block diagram illustration of an image processor forming part of the system of FIG. 1. An image slicer 50, typically embodied in software, is operative to reslice an image of a three-dimensional object, such as a body part stored in computer memory. This reslicing is clearly not necessarily parallel to or coextensive with the two-dimensional slices acquired by the imager 30 (FIG. 2).

In a preferred embodiment of the present invention shown in FIG. 4, the three-dimensional image input to the image slicer 50 is received from the image constructor 36 (FIG. 2), a preferred embodiment of which is shown in FIG. 3.

The output of image slicer 50 is supplied to an edge enhancer and/or edge detector 52, which is preferably embodied in software. A preferred embodiment of an edge enhancer and/or detector 52 is described in applicant's U.S. patent applications Ser. No. 09/351,252 filed Jul. 12, 1999 and Ser. No. 09/352,002 filed Jul. 12, 1999, the disclosures of which are hereby incorporated by reference, with reference to FIGS. 13A, 13B and 17. Other edge enhancement procedures are also found in "Digital Picture Processing", by Azriel Rosenfeld and Avinash C. Kak, Vol. 2, pp. 84–112, second edition, published by Academic Press, USA, 1982, the disclosure of which is hereby incorporated by reference. An edge detected image can be obtained from the edge enhanced image by applying thresholding. However, the optional manual intervention is described in applicant's U.S. patent applications Ser. No. 09/351,252 filed Jul. 12, 1999 and Ser. No. 09/352,002 filed Jul. 12, 1999, the disclosures of which are hereby incorporated by reference, with reference to FIGS. 12–19. The edge enhancer and/or edge detector provides a digital output representing enhanced edges in a two-dimensional image slice or only the edges without the remaining image information.

The output of edge enhancer and/or detector 52 is supplied to a three-dimensional image reconstructor 54, which is operative to combine the outputs of edge enhancer and/or detector 52 for multiple two-dimensional slices, into a three-dimensional output. A preferred embodiment of a 3D surface reconstructor from contours, which may originate from 2D edge detection, is described in "Surface Interpolation from Sparse Cross-Sections Using Region Correspondence", G. M. Treece, R. W. Prager, A. H. Gee and L. Berman, CUED/F-INTEG/TR 342, March 1999, Cambridge University Engineering Department, Trumpington Street, Cambridge CB2 1PZ, England, the disclosure of which is hereby incorporated by reference.

The output of three-dimensional image reconstructor 54 is supplied to a model fitter 56 which is operative to customize a generalized geometrical model to fit the data received from the reconstructor 54. The operation of the model fitter 56 is preferably entirely automatic, based on preset user supplied parameters, but may, alternatively, employ certain user control inputs, which may be provided by an optional user interface 58. The operation of a preferred embodiment of model fitter 56 is described hereinbelow in greater detail with reference to FIG. 9.

The output of model fitter 56 is supplied to a model based edge refiner 60, preferably embodied in software, which is operative to select the most relevant edges in the output of reconstructor 54 with respect to their relationship with the model which was fitted thereto. The edge refiner 60 also is operative to extrapolate and/or interpolate relevant edges in image regions where the output of edge enhancer and/or detector is insufficient, such as due to limitations in the acquisition of ultrasound image data.

For example, the edge refiner 60 discards edge data which is outside a region of interest defined using the output of the model fitter 56.

The output of the model based edge refiner 60 is supplied to a model based body part identifier 62, which is preferably embodied in software. Identifier 62 is operative to isolate and extract predetermined body parts from the overall image, typically received from reconstructor 54. The functionality of identifier 62 is to identify in the overall image, known body parts, whose size is to be measured.

The output of identifier 62 is supplied to a measurement tool 64, preferably embodied in software. The measurement tool 64 is preferably operative to obtain size parameters from the output of identifier 62 with respect to one or more body parts, whose size parameters have a known relationship to fetal weight. Measurement tool 64 may include a tissue characterization processor, which provides data relating to the percentages of different types of tissue in the fetus. Additionally, the measurement tool 64 is preferably operative without requiring user input during measurement.

The output of measurement tool 64 is supplied to a volume/weight calculator 66, typically embodied in software, which employs the output of measurement tool 64, alone or in combination with other parameters and/or archival data to provide an output indication of at least one of fetal volume and fetal weight. Calculator 66 may operate in accordance with one or more conventional formulae for calculation of fetal weight and/or volume.

Figure 5:
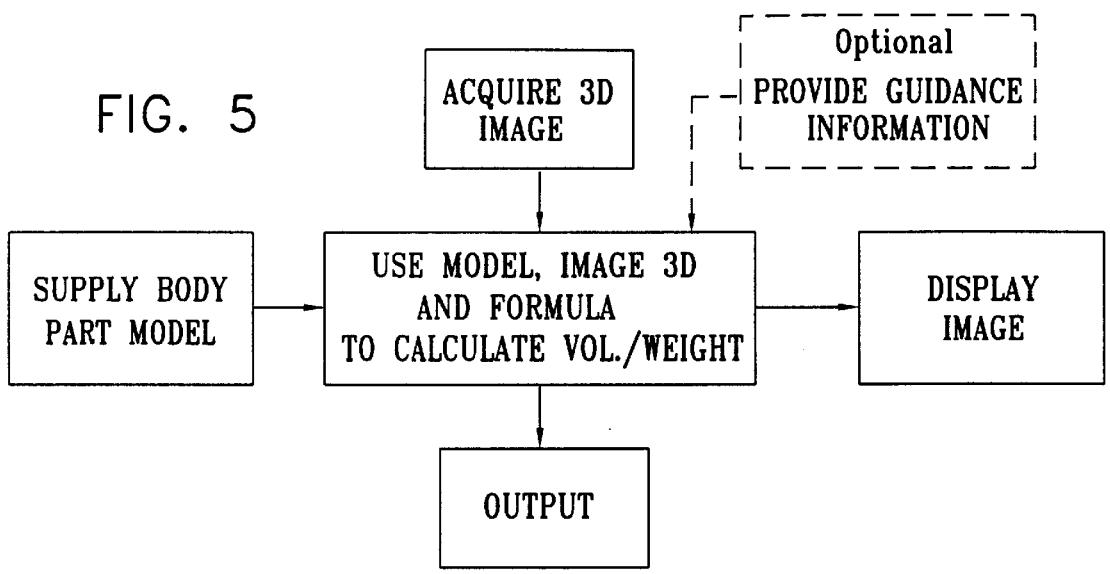
FIG. 5 is a simplified flow chart illustrating operation of the system of FIG. 1.

Reference is now made to FIG. 5, which is a simplified flow chart illustrating operation of the system of FIG. 1. As seen in FIG. 5, a three-dimensional image of a fetus as well as at least one generalized body part model are employed for automatically calculating body weight and volume. Optionally, user inputs may provide guidance for the automatic functionality. The fetal body weight and/or volume may be output in alphanumeric form and an image of the fetus or of selected body parts thereof may also be displayed.

Figure 6:
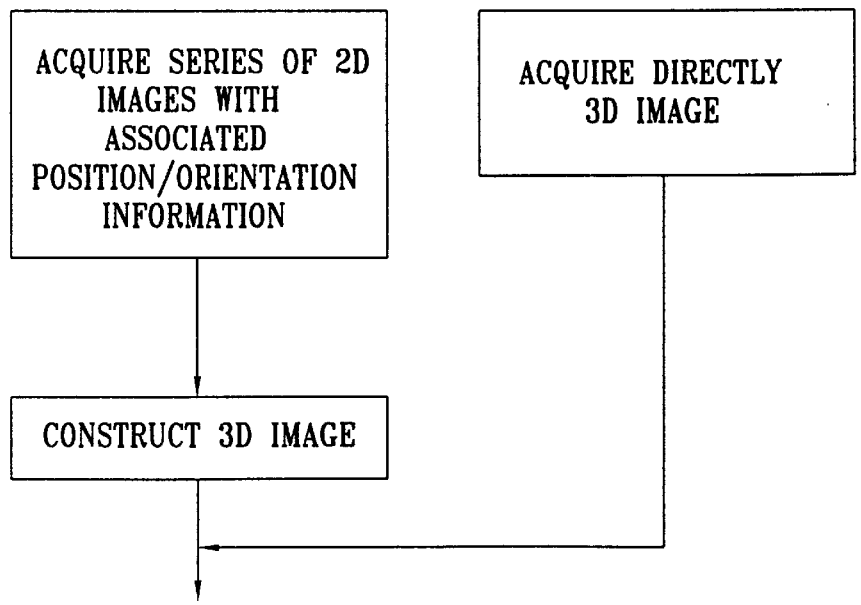
FIG. 6 is a simplified flow chart of an image acquiring step forming part of the functionality of FIG. 5.

FIG. 6 is a simplified flow chart of an image acquiring step forming part of the functionality of FIG. 5. FIG. 6 clearly indicates that acquisition of the three-dimensional image may be realized either by direct acquisition of a three-dimensional image or alternatively by acquisition of a series of two-dimensional images and construction of a three-dimensional image therefrom.

Figure 7:
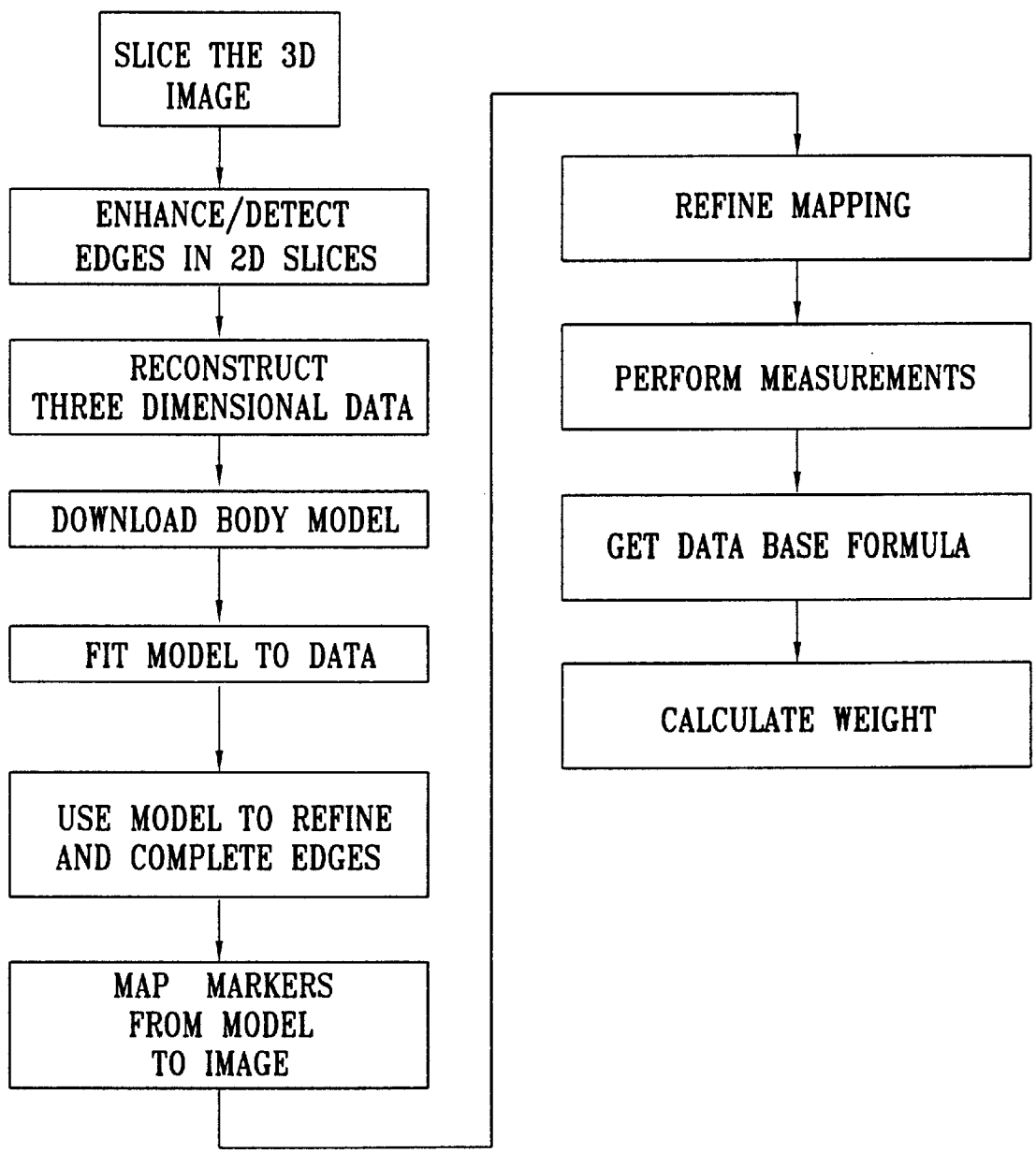
FIG. 7 is a simplified flow chart of a weight calculation step forming part of the functionality of FIG. 5.

Reference is now made to FIG. 7, which is a simplified flow chart of a weight calculation step forming part of the functionality of FIG. 5. As seen in FIG. 7, a three-dimensional image is sliced and edges are enhanced and/or detected in the resulting two-dimensional slices. Preferred methodologies for edge enhancement are described in U.S. patent applications Ser. No. 09/351,252 filed Jul. 12, 1999 and Ser. No. 09/352,002 filed Jul. 12, 1999, the disclosures of which are hereby incorporated by reference. The edge enhanced image data or edge data from the two-dimensional slices are combined to reconstruct three-dimensional data.

A body model is then retrieved from storage. Generation of the body model is described hereinbelow with reference to FIG. 9. The body model is customized to fit the reconstructed three-dimensional data. The customized body model is then employed to refine and complete edges of body parts. Thus it may be appreciated that the final outline is based on image edge data where such exists and upon the body model where image data is either unclear or does not exist.

At this stage, the volume of the entire fetus may be calculated from an outline of the entire fetus and this volume may be multiplied by a density known from the literature to provide an indication of body weight. This procedure, although simple, is not preferred due to inherent inaccuracies therein.

A significant improvement to this procedure may be obtained by calculating the density of each individual fetal part rather than using the standard body density taken from the literature. The weight of the individual fetal part is then calculated by multiplying the individual fetal part density by the fetal part volume. This improvement is achieved whenever the calculated individual density approximates the actual fetal part density more closely than the standard body density as found in the literature.

In the improved method of determining fetal weight it is necessary to determine the density of each fetal part. This is carried out by first performing a tissue characterization or classification to define each pixel of the body image, as a fetal fluid, fetal bone, fetal soft tissue (fat or muscle) or undefined and associate a corresponding density with each of these fetal body components.

In order to classify each pixel, one may consider a pixel 3×3 window (or a 3×3×3 voxel window in 3-dimensions) centered at that pixel and consider the average image intensity and the standard deviation (SD) of the image intensity within the window. The tissue classification is based upon comparing the average intensity and the SD with given threshold values, as defined hereinbelow.

If the average image intensity is below a given threshold S1 (average<S1) then the pixel represents fluid.

If the average image intensity is above a given threshold S2 and the condition (SD/average) is smaller than a given threshold S3, then the pixel represents bone.

If the average image intensity is between given thresholds S4 and S5 and the SD is above a given threshold S6, then the pixel represents soft tissue.

A pixel, which does not fulfill any of these conditions, is said to be undefined and is not taken into consideration, as described hereinbelow.

The determination of the thresholds S1, S2, S3, S4, S5 and S6 may be found experimentally by setting the values of S1, S2, S3, S4, S5 and S6, such that the classification based upon these threshold values would best fit actual image classifications of sample images in which the components are classified manually, as is known in the art.

A further method for determining the tissue classification may be found in "Two-Dimensional and Three-Dimensional Tissue-Type Imaging of the Prostate Based on Ultrasonic Spectrum Analysis and Neural-Network Classification", Ernest J. Feleppa et al., Medical Imaging 2000: Ultrasonic Imaging and Signal Processing, Editors K. Kirk Shung and Michael F. Insana, Feb. 16–17, 2000, San Diego, Calif., Proc. of SPIE Volume 3982 (2000), the disclosure of which is hereby incorporated by reference.

Let N1, N2 and N3 be the number of fluid, bone and tissue pixels, respectively, and N=N1+N2+N3. Let D1, D2 and D3 be the densities, as found in the literature, of fluid, bone and tissue, respectively. Thus, the density of the individual fetus D, may be determined by the weighted average:

$$D=(D1*N1/N)+(D2*N2/N)+(D3*N3/N).$$

In accordance with a preferred embodiment of the present invention, markers incorporated within the body model, which indicate sizes of certain body parts which are indicative of body weight, are mapped onto the reconstructed three-dimensional image data. An example of one such size is femur length. The positions of the mapped markers are then refined by employing edge outline information, as described hereinbelow.

Figure 8B:
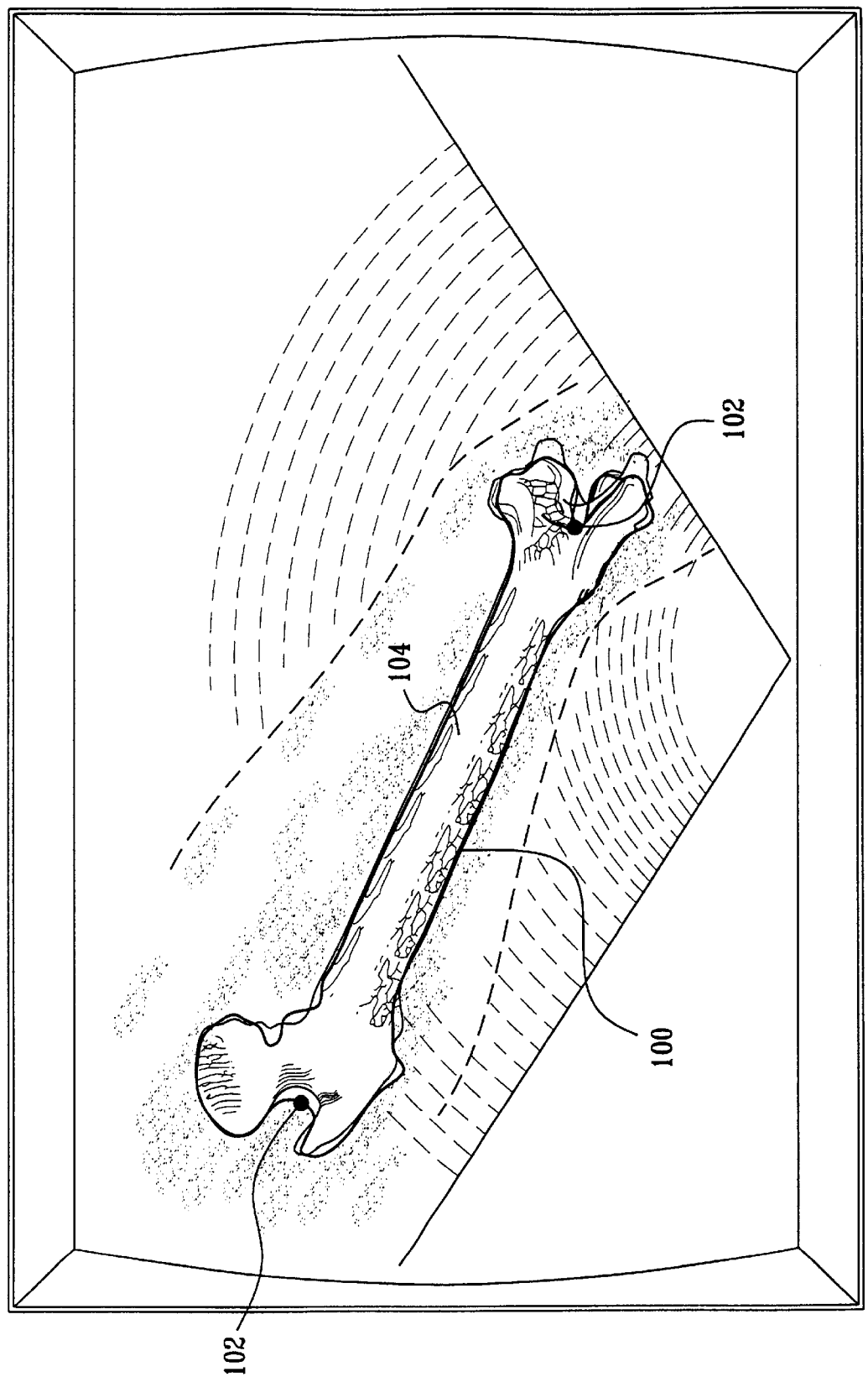
Figure 8C:
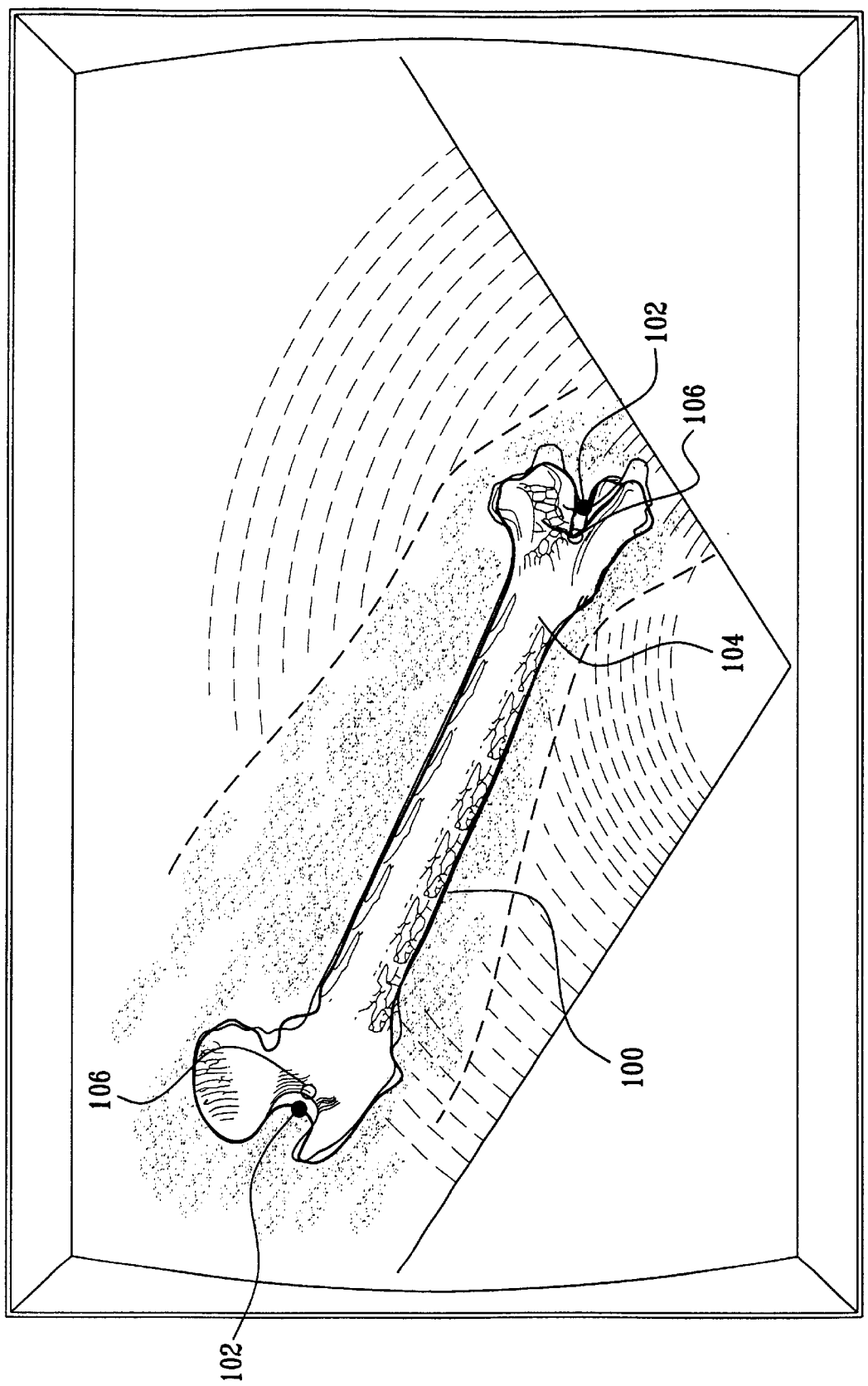

Reference is now to FIGS. 8A, 8B and 8C which illustrate typical steps useful in the mapping of a femur model 100 and markers 102 onto an ultrasound image of a femur bone 104. In this example, typical steps for determining femur weight include fitting a femur model 100 with markers 102 to the femur image 104 (FIG. 8A), fitting model 100 with markers 102 on to the femur image 104 to obtain the model shown in FIG. 8B, wherein the markers 102 are shown as being mapped on to the image 104. FIG. 8C shows the results of refining the position of the markers 102 to fit the edges of the image 104 so as to reposition their appropriate final location 106.

Measurements are then performed employing the markers to provide size indications of one or more body parts and conventional formulae, preferably stored in a data base, are employed for calculating body weight therefrom. Suitable formulae for this purpose may be found in "Quantitative Obstetrical Ultrasonography", Russell L. Deter et al., pp 115–116, published by John Wiley & Sons, 1986, the disclosure of which is hereby incorporated by reference. In a specific example, the markers are located at the ends of the femur, the length of the femur is calculated by measuring the distance between the markers and the fetal weight is determined from the femur length by employing conventional formulae in an automatic manner.

Figure 9:
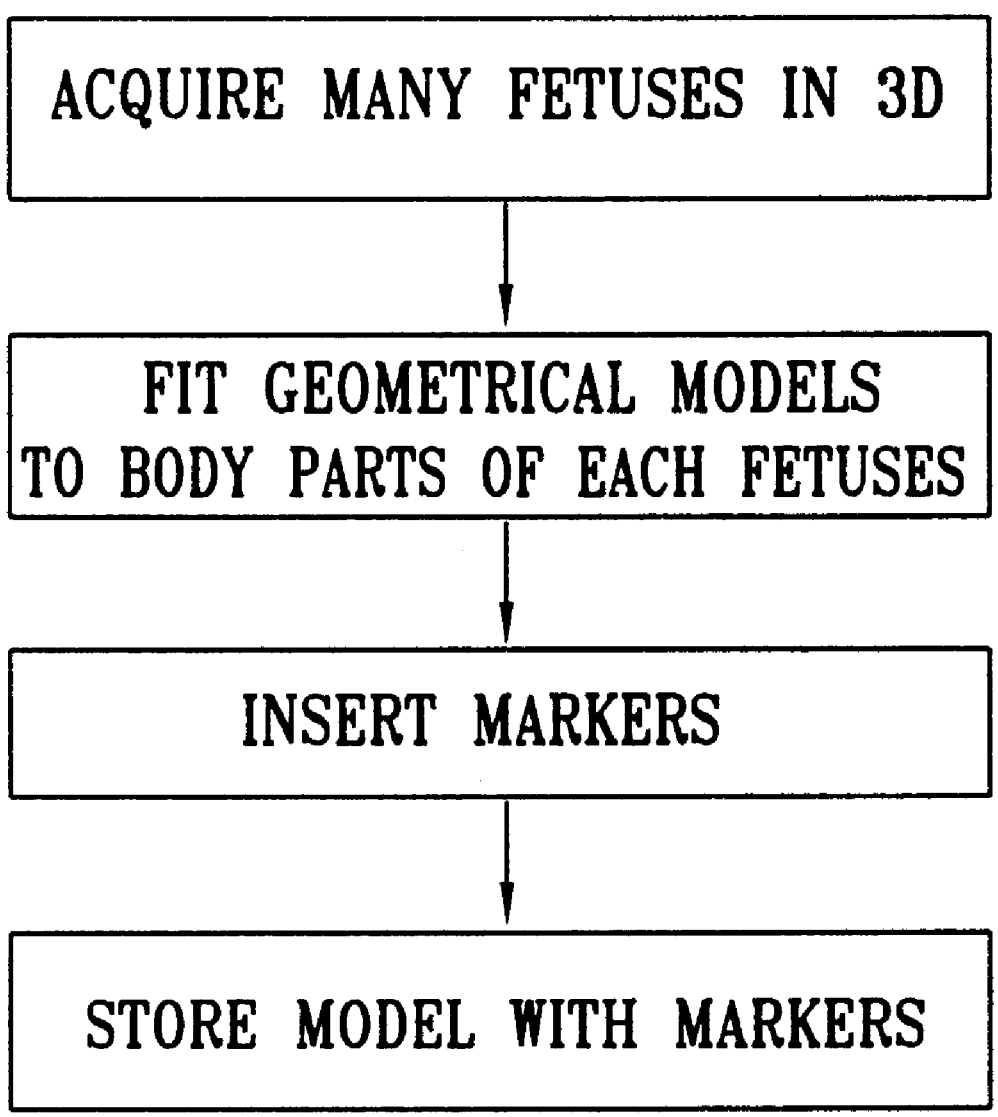
FIG. 9 is a simplified flow chart of a body modeling step forming part of the functionality of FIG. 5.

Reference is now made to FIG. 9, which is a simplified flow chart of a body model generating step employed to provide a body model which is employed in the functionality of FIGS. 5 and 7.

The body model generating step is based on statistically valid sampling of three-dimensional image data of multiple fetuses. A three-dimensional geometric model is fitted to each body part of each fetus. Typical geometrical models include ellipsoids and quadratic surfaces and portions thereof.

One or two dimensional markers are preferably inserted within each geometrical model to indicate sizes which have significance in determining fetal weight.

The geometrical models and the markers are then temporarily stored and combined with suitable weighting to define a body model, which is stored for download in the functionality of FIGS. 5 and 7.

Figure 10:
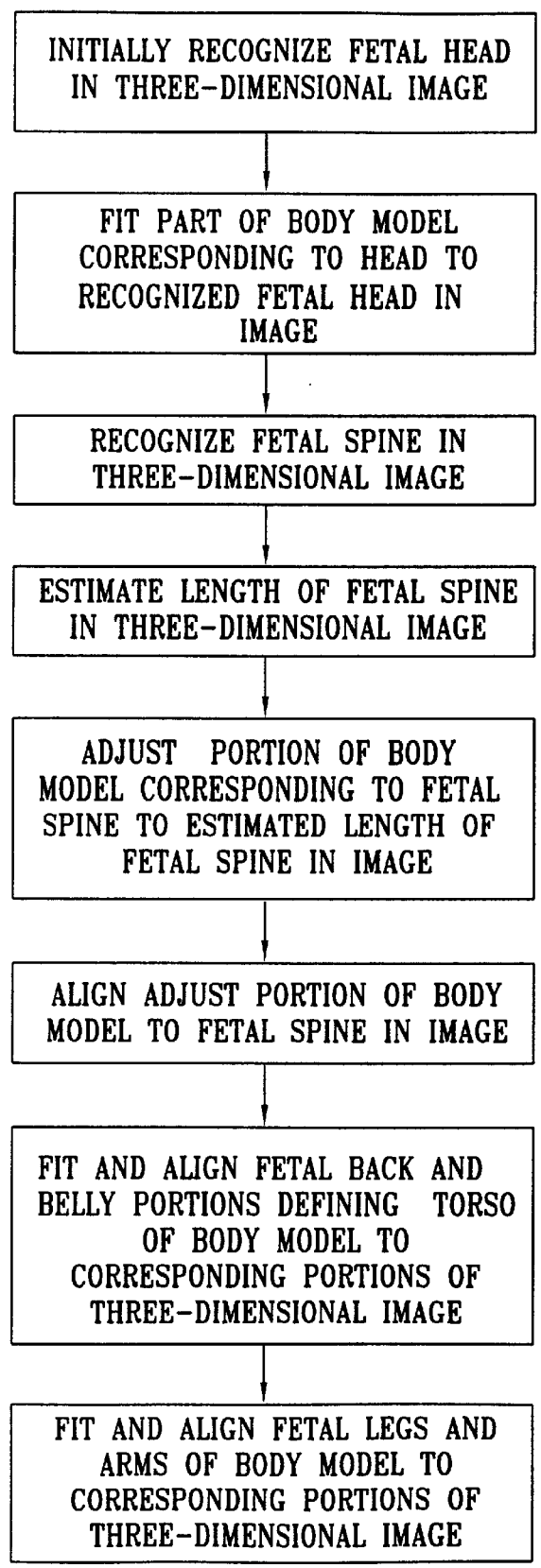
FIG. 10 is a simplified flow chart of a body model fitting step forming part of the functionality of FIG. 5.

Reference is now made to FIG. 10, which is a simplified flow chart of a body model fitting step forming part of the functionality of FIG. 5. Preferably the head of the fetus is initially recognized in the image and the part of the body model corresponding to the head, typically an ellipsoid, is fitted to the corresponding part of the image. This initial step may employ techniques described in U.S. Pat. No. 5,605,155, the disclosure of which is hereby incorporated by reference. Preferably, upon initial recognition of the head of the fetus in the image, edge enhancement is performed to better define the outline of the head of the fetus. Optionally, the head portion of the image may be converted to a binary image so as to further define the outline of the fetal head.

Following fitting of the head portion, the fetal spine is recognized in the image and the length of the fetal spine is estimated by finding the ends of the fetal spine in the image. The portion of the body model corresponding to the fetal spine is adjusted to the estimated length of the fetal spine in the image and the portion of the body model corresponding to the fetal spine is then aligned with the fetal spine in the image.

Thereafter the fetal back and belly portions defining the torso of the body model are fitted to the corresponding portions of the image, followed by the legs and arms.

Figure 11:
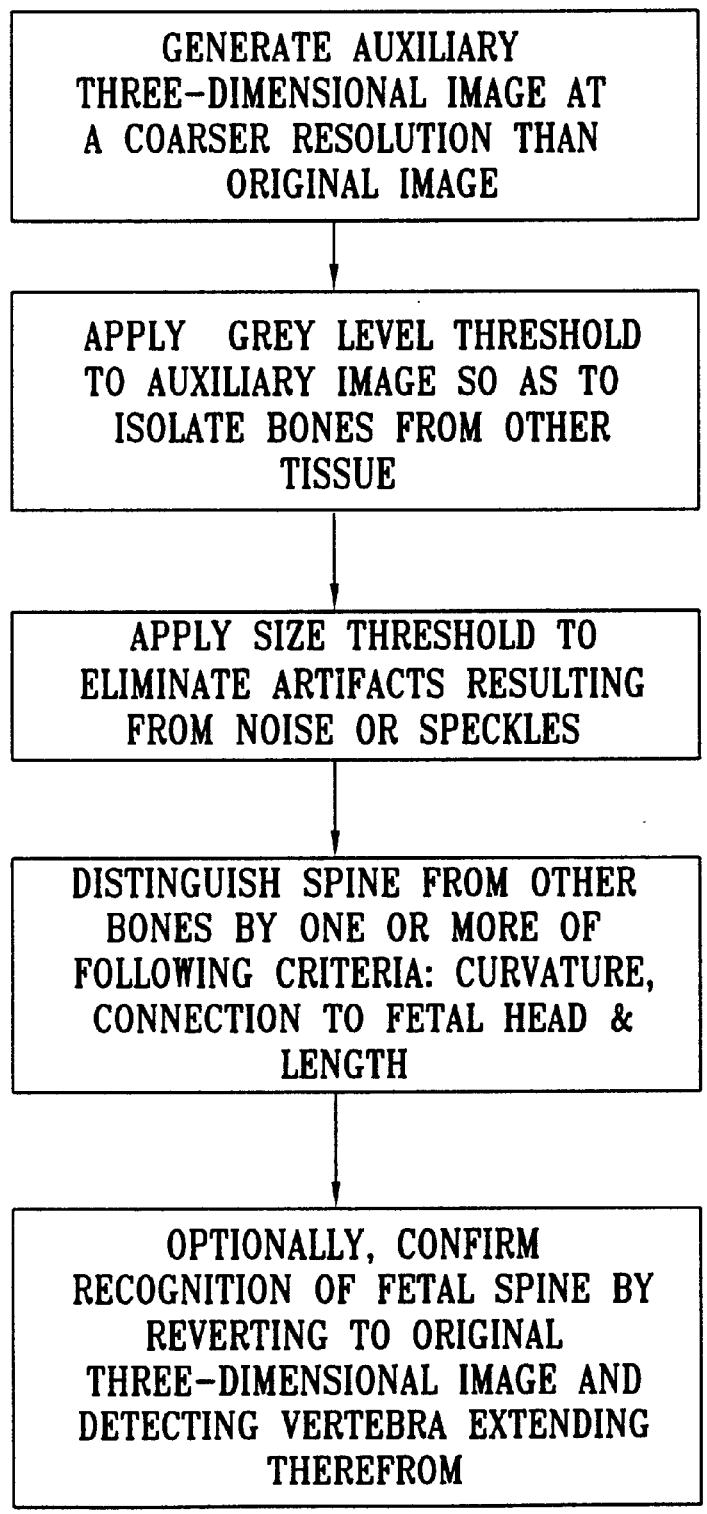
FIG. 11 is a simplified flow chart illustrating a technique for recognizing a fetal spine in a three-dimensional image.

Reference is now made to FIG. 11 which describes a preferred technique for fetal spine recognition in a three-dimensional image. Preferably, an auxiliary three-dimensional image is provided at a coarser resolution than that of the original image. A grey level threshold is applied to the auxiliary image so as to isolate bones from other tissue. A size threshold is also preferably applied to eliminate artifacts resulting from noise or speckles.

The spine may then be recognized in the thresholded auxiliary image and distinguished from other bones in the fetus by looking for low, but not lowest curvature, a connection at one end to the fetal head and a length within a predetermined range of an expected fetal spine length.

Optionally, detection of the fetal spine in the relatively coarse resolution image may be confirmed by reverting to the original image and recognizing therein vertebra extending outwardly from the spine. A preferred technique for recognizing vertebra is described hereinbelow with reference to FIG. 12.

Figure 12:
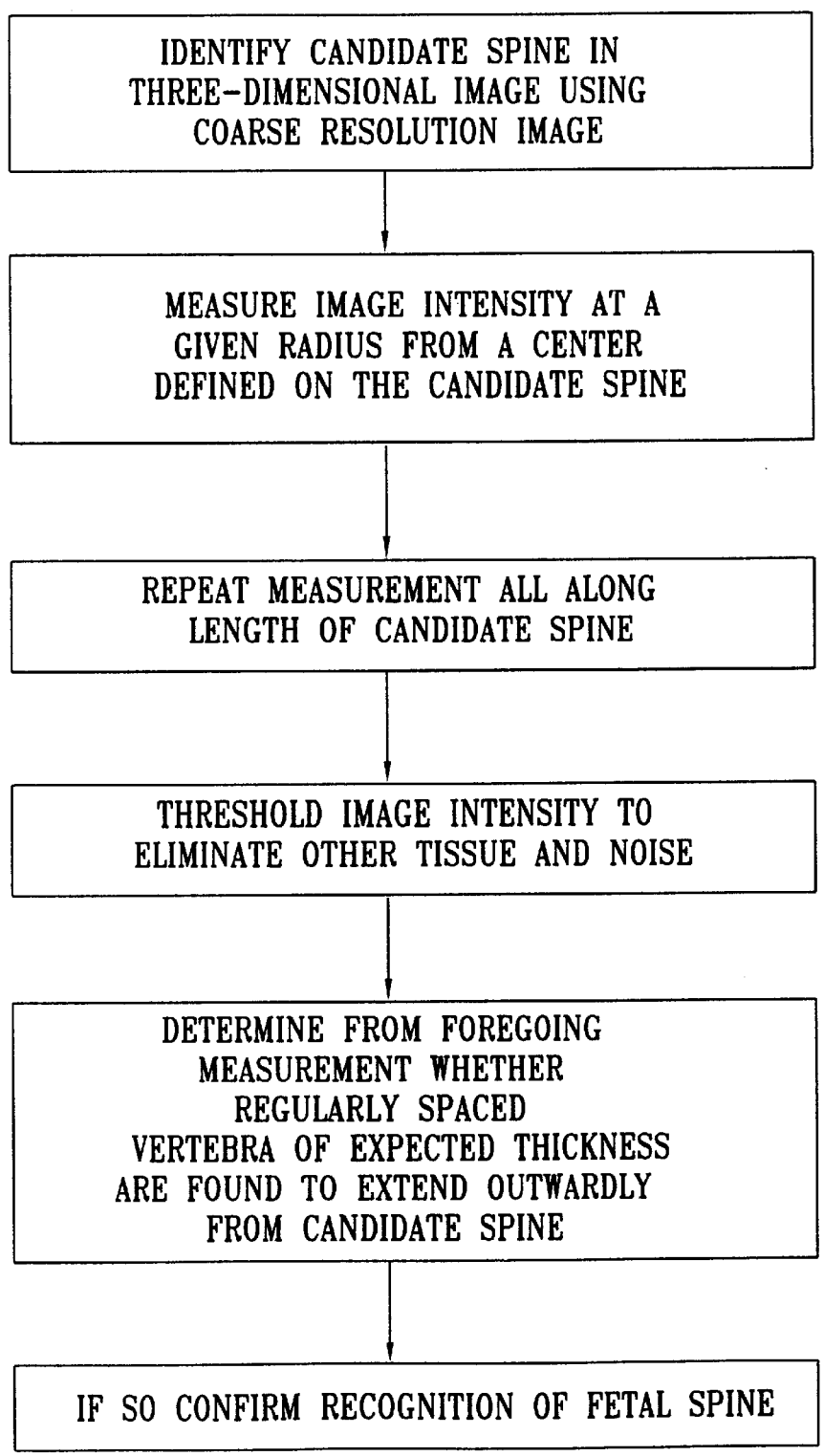
FIG. 12 is a simplified flow chart illustrating a technique for confirming the existence of vertebra in a fetal spine, useful in the technique of FIG. 11.

As seen in FIG. 12, a candidate spine may be identified from the coarse resolution image. The image intensity is measured at a given radius measured from a center defined on the candidate spine. Such measurements are taken all along the length of the spine to determine whether regularly spaced vertebra extend outwardly from the candidate spine. Suitable thresholding is applied to the results of the measurement to detect the vertebra and distinguish them from other tissue or noise. If a pattern corresponding to the spacing and thickness of typical vertebra along a fetal spine is found, then detection of the spine is confirmed.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specification and which are not in the prior art.

What is claimed is:

1. Apparatus for fetal weight determination comprising:
    an ultrasonic imager operative to image a fetus in utero and to provide output image data in respect thereof;
    an image processor operative automatically to initially recognize and then to measure at least one dimension of at least one fetal body part based on said output image data and to provide output body part dimension data; and
    an automatic fetal weight calculator operative to calculate fetal weight automatically based on said output body part dimension data.

2. Apparatus for fetal weight determination according to claim 1 and wherein said image processor is operative automatically to fit a three-dimensional model to said three-dimensional output image data, thereby to compensate for missing image data in said three-dimensional output image data.

3. Apparatus for distinguishing a fetus in a three-dimensional ultrasound image of the fetus in utero, said apparatus comprising:
    an ultrasonic imager operative to image a fetus in utero and to provide three-dimensional output image data in respect thereof; and
    an image processor operative automatically to initially recognize and then to distinguish the fetus from surrounding tissue based on said output image data.

4. Apparatus for recognition of a fetal spine in an ultrasound image of the fetus in utero, said apparatus comprising:
    an ultrasonic imager operative to image a fetus in utero and to provide output image data in respect thereof; and
    an image processor operative automatically to recognize the fetal spine from surrounding tissue based on said output image data.

5. Apparatus according to claim 4 and wherein said image processor is also operative to measure the length of the fetal spine.

6. Apparatus for automatically fitting a three-dimensional model of a fetus to a three-dimensional ultrasound image of the fetus in utero, said apparatus comprising:
    an ultrasonic imager operative to image a fetus in utero and to provide three-dimensional output image data in respect thereof; and an image processor operative automatically to initially recognize and then to fit said three-dimensional model to said three-dimensional output image data.

7. Apparatus for automatically fitting a three-dimensional model of a fetus to a three-dimensional ultrasound image of the fetus in utero according to claim 6 and wherein said image processor is operative automatically to fit portions of said three-dimensional model to corresponding portions of said three-dimensional output image data.

8. Apparatus according to claim 7 and wherein said image processor is also operative to provide mapping of anatomical markers from said model onto said output image data and to carry out measurements using said anatomical markers.

9. Apparatus for automatically fitting a three-dimensional model of a fetal torso to a three-dimensional ultrasound image of the fetus in utero according to claim 6 and wherein said image processor is operative automatically to fit portions of said three-dimensional model of a fetal torso to corresponding portions of said three-dimensional output image data.

10. Apparatus according to claim 9 and wherein said image processor is also operative to provide mapping of anatomical markers from said model onto said output image data and to carry out measurements using said anatomical markers.

11. Apparatus according to claim 6 and wherein said image processor is also operative to provide mapping of anatomical markers from said model onto said output image data and to carry out measurements using said anatomical markers.

12. Apparatus for automatically fitting a three-dimensional model of a fetus to a three-dimensional ultrasound image of the fetus in utero, said apparatus comprising:

an image processor operative automatically to initially recognize and then to fit portions of said three-dimensional model to corresponding portions of said three-dimensional output image data.

13. Apparatus according to claim 12 and wherein said image processor is also operative to provide mapping of anatomical markers from said model onto said output image data and to carry out measurements using said anatomical markers.

14. Apparatus for automatically fitting a three-dimensional model of a fetal torso to a three-dimensional ultrasound image of the fetus in utero, said apparatus comprising:

an ultrasonic imager operative to image a fetus in utero and to provide three-dimensional output image data in respect thereof; and an image processor operative automatically to fit said three-dimensional model of a fetal torso to said three-dimensional output image data.

15. Apparatus according to claim 14 and wherein said image processor is also operative to provide mapping of anatomical markers from said model onto said output image data and to carry out measurements using said anatomical markers.

16. Apparatus for automatically fitting a three-dimensional model of a fetal torso to a three-dimensional ultrasound image of the fetus in utero, said apparatus comprising:

an image processor operative automatically to fit portions of said three-dimensional model of fetal torso to corresponding portions of said three-dimensional output image data.

17. Apparatus according to claim 16 and wherein said image processor is also operative to provide mapping of anatomical markers from said model onto said output image data and to carry out measurements using said anatomical markers.

18. Apparatus for fetal volume determination comprising:

an ultrasonic imager operative to image a fetus in utero and to provide output image data in respect thereof;

an image processor operative automatically to initially recognize and then to measure at least one dimension of at least one fetal body part based on said output image data and to provide output body part dimension data; and an automatic fetal volume calculator operative to calculate fetal volume automatically based on said output body part dimension data.

19. Apparatus for fetal weight determination comprising:

an ultrasonic imager operative to image a fetus in utero and to provide output image data in respect thereof;

an image processor operative automatically to measure at least one dimension of at least one fetal body part based on said output image data and to provide output body part dimension data;

a tissue characterization processor employing said output image data for providing data relating to percentages of different types of tissue in at least part of said fetus; and an automatic fetal weight calculator operative to calculate fetal weight automatically based on said output body part dimension data and said data relating to percentages of different types of tissue in at least part of said fetus.

20. A method for determining fetal weight comprising:

employing an ultrasonic imager to image a fetus in utero and to provide output image data in respect thereof;

identifying at least one body part from said image data;

employing an image processor to automatically initially recognize and then to measure at least one dimension of at least one fetal body part based on said output image data and to provide output body part dimension data; and calculating fetal weight automatically based on said output body part dimension data.

21. A method for fetal weight determination according to claim 20 and wherein said image processor is operative automatically to fit a three-dimensional model to said three-dimensional output image data, thereby to compensate for missing image data in said three-dimensional output image data.

22. A method for distinguishing a fetus in a three-dimensional ultrasound image of the fetus in utero, the method comprising:

employing an ultrasonic imager to image a fetus in utero and to provide three-dimensional output image data in respect thereof; and providing an image processor to automatically initially recognize and then to distinguish the fetus from surrounding tissue based on said output image data.

23. A method for recognizing a fetal spine in an ultrasound image of the fetus in utero, said method comprising:

operating an ultrasonic imager to image a fetus in utero and to provide output image data in respect thereof; and providing an image processor to automatically recognize the fetal spine from surrounding tissue based on said output image data.

24. A method according to claim 23 and wherein said image processor also operates to measure the length of the fetal spine.

25. A method for automatically fitting a three-dimensional model of a fetus to a three-dimensional ultrasound image of the fetus in utero, said method comprising:

employing an ultrasonic imager to image a fetus in utero and to provide three-dimensional output image data in respect thereof;

providing a three-dimensional model; and employing an image processor to automatically initially recognize and then fit said three-dimensional model to said three-dimensional output image data.

26. A method according to claim 25 and wherein said image processor also operates to provide mapping of anatomical markers from said model onto said output image data and to carry out measurements on said output image data using said anatomical markers.

27. A method for automatically fitting a three-dimensional model of a fetus to a three-dimensional ultrasound image of the fetus in utero, said method comprising:

operating an image processor to automatically initially recognize and then to fit portions of said three-dimensional model to corresponding portions of said three-dimensional output image data.

28. A method according to claim 27 and wherein said image processor also operates to provide mapping of anatomical markers from said model onto said output image data and to carry out measurements on said output image data using said anatomical markers.

29. A method for automatically fitting a three-dimensional model of a fetus to a three-dimensional ultrasound image of the fetus in utero according to claim 25 and wherein said image processor operates to automatically fit portions of said three-dimensional model to corresponding portions of said three-dimensional output image data.

30. A method according to claim 29 and wherein said image processor also operates to provide mapping of anatomical markers from said model onto said output image data and to carry out measurements on said output image data using said anatomical markers.

31. A method for automatically fitting a three-dimensional model of a fetal torso to a three-dimensional ultrasound image of the fetus in utero, said method comprising:

employing an ultrasonic imager to image a fetus in utero and to provide three-dimensional output image data in respect thereof; and employing an image processor to automatically fit said three-dimensional model of a fetal torso to said three-dimensional output image data.

32. A method according to claim 31 and wherein said image processor also operates to provide mapping of anatomical markers from said model onto said output image data and to carry out measurements on said output image data using said anatomical markers.

33. A method for automatically fitting a three-dimensional model of a fetal torso to a three-dimensional ultrasound image of the fetus in utero, said method comprising:

operating an image processor to automatically fit portions of said three-dimensional model of fetal torso to corresponding portions of said three-dimensional output image data.

34. A method according to claim 33 and wherein said image processor also operates to provide mapping of anatomical markers from said model onto said output image data and to carry out measurements on said output image data using said anatomical markers.

35. A method for automatically fitting a three-dimensional model of a fetal torso to a three-dimensional ultrasound image of the fetus in utero according to claim 25 and wherein said image processor operates to automatically fit portions of said three-dimensional model of a fetal torso to corresponding portions of said three-dimensional output image data.

36. A method according to claim 35 and wherein said image processor also operates to provide mapping of anatomical markers from said model onto said output image data and to carry out measurements on said output image data using said anatomical markers.

37. A method for fetal volume determination comprising:

operating an ultrasonic imager to image a fetus in utero and to provide output image data in respect thereof;

identifying at least one individual fetal body part from said image data;

providing an image processor to automatically initially recognize and then to measure at least one dimension of at least one fetal body part based on said output image data and to provide output body part dimension data; and providing an automatic fetal volume calculator to calculate fetal volume automatically based on said output body part dimension data.

38. A method for fetal weight determination comprising:

employing an ultrasonic imager to image a fetus in utero and to provide output image data in respect thereof;

identifying at least one individual fetal body part from said image data;

employing an image processor to automatically measure at least one dimension of at least one fetal body part based on said output image data and to provide output body part dimension data;

providing a tissue characterization processor employing said output image data for providing data relating to percentages of different types of tissue in at least part of said fetus; and operating an automatic fetal weight calculator to calculate fetal weight automatically based on said output body part dimension data and said data relating to percentages of different types of tissue in at least part of said fetus.

* * * * *